United States Patent
Xia et al.

(10) Patent No.: US 12,012,628 B2
(45) Date of Patent: Jun. 18, 2024

(54) METHOD TO ELEVATE THE AMOUNT OF STEVIOL GLYCOSIDES REMAINED IN THE RECRYSTALLIZATION MOTHER LIQUOR OF STEVIA EXTRACT

(71) Applicant: Jiangnan University, Wuxi (CN)

(72) Inventors: Yongmei Xia, Wuxi (CN); Zhuoyu Zhou, Wuxi (CN); Ye Fan, Wuxi (CN); Xueyi Hu, Wuxi (CN); Yun Fang, Wuxi (CN); Xiang Liu, Wuxi (CN); Haijun Wang, Wuxi (CN); Jing Wu, Wuxi (CN); Fei Xu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 874 days.

(21) Appl. No.: 17/105,781

(22) Filed: Nov. 27, 2020

(65) Prior Publication Data
US 2021/0079437 A1 Mar. 18, 2021

Related U.S. Application Data

(63) Continuation of application No. PCT/CN2019/090911, filed on Jun. 12, 2019.

(30) Foreign Application Priority Data

Dec. 4, 2018 (CN) .......................... 201811472667.6

(51) Int. Cl.
*C12P 19/56* (2006.01)
*A23L 27/30* (2016.01)
*C12P 19/14* (2006.01)

(52) U.S. Cl.
CPC .............. *C12P 19/56* (2013.01); *A23L 27/36* (2016.08); *C12P 19/14* (2013.01); *A23V 2002/00* (2013.01)

(58) Field of Classification Search
None
See application file for complete search history.

(56) References Cited

FOREIGN PATENT DOCUMENTS

| CN | 109651453 A | 4/2019 |
| WO | 2014185931 A1 | 11/2014 |

OTHER PUBLICATIONS

Nguyen, Thi Thanh; et al; "Production of rubusoside from stevioside by using a thermostable lactase from Thermus thermophilus and solubility enhancement of liquiritin and teniposide" Enzyme and Microbial Technology, 64, 38-43, 2014 (Year: 2014).*

Mahoney, RR; et al; "Selection of Strain, Growth Conditions, and Extraction Procedures for Optimum Production of Lactase from Kluyveromyces fragilis" Journal of Dairy Science, 58, 1620-1629, 1975 (Year: 1975).*

Santos, A; et al; "Kinetic modeling of lactose hydrolysis [beta]-galactosidase from Kluyveromices fragilis" Enzyme and Microbial Technology, 22, 558-567, 1998 (Year: 1998).*

* cited by examiner

*Primary Examiner* — David W Berke-Schlessel
(74) *Attorney, Agent, or Firm* — IPRO, PLLC

(57) ABSTRACT

The disclosure discloses a method to elevate the amount of steviol glycosides remained in the recrystallization mother liquor of *Stevia* extract, and belongs to the field of modification and extraction of natural compounds. The disclosure adopts lactase for highly specific catalytic hydrolysis of stevioside to convert stevioside into rubusoside which usually can only be obtained from leaves of *Rubus suavissimus* S. Lee; and meanwhile, after stevioside in the mother liquor glycosides is converted, since the polarity difference between rubusoside and rebaudioside A is far larger than the polarity difference between stevioside and rebaudioside A, rebaudioside A is more easily separated out of the mother liquor glycosides. A technology provided by the disclosure is also applicable to value increment of mixed steviol glycosides containing stevioside and is beneficial for separating out rebaudioside A from the mixed steviol glycosides.

12 Claims, 4 Drawing Sheets

METHOD TO ELEVATE THE AMOUNT OF STEVIOL GLYCOSIDES REMAINED IN THE RECRYSTALLIZATION MOTHER LIQUOR OF STEVIA EXTRACT

TECHNICAL FIELD

The disclosure relates to a method to elevate the amount of steviol glycosides remained in the recrystallization mother liquor of *Stevia* extract, relates to value increment utilization of mother liquor glycosides and mixed steviol glycosides generated after extraction and purification of steviol glycosides, and belongs to the field of modification and separation of natural compounds.

BACKGROUND

*Stevia* sugar, as a mixture of various steviol glycosides, is referred to steviol glycoside, and it is an ideal saccharose substitute sweetener extracted from *Stevia rebaudiana*. The unrefined steviol glycosides generally contain 80% or more total steviol glycosides, usually 50 wt % or more rebaudioside A (RA) and 25-30 wt % of stevioside (St). In which, rebaudioside A has a good taste but expensive, about 4 folds to that of unrefined steviol glycosides or 5 folds to that of *Stevia* mother liquor glycosides. *Stevia* mother liquor glycosides are by-products from the extracting and processing process of the *Stevia*, which possess a very poor taste, and still contain a total amount of 50% or more stevioside and rebaudioside A. Due to the low polarity difference between stevioside and rebaudioside A, it is relatively difficult to further separate out high-value rebaudioside A from the *Stevia* mother liquor, thus the *Stevia* mother liquor glycosides can only be sold at a price less than one quarter of that of RA.

A production process of steviol glycosides includes leaf smashing, soaking and extracting, flocculating, preliminary decoloring, adsorbing, membrane filtering, crystallizing and refining, concentrating, drying, recrystallizing and drying. After the first crystallizing and drying, steviol glycosides with different compositions are obtained, which is referred to as mixed glycosides in industry; and the relatively-pure steviol glycosides, such as 60-97% of RA, can then be obtained through adsorbing separation with macroporous resin or recrystallizing separation of the mixed glycosides. After the recrystallizing separation, the crystallized steviol glycosides have a relatively-high content of single components such as RA or St, and the mixed glycosides left in mother liquor are dried to obtain glycosides with complex composition, which are referred to as mother liquor glycosides in industry.

More than half of the steviol glycosides in the mother liquor glycosides are still rebaudioside A and stevioside; but it has been relatively difficult to further separate out and extract rebaudioside A and stevioside from the mother liquor glycosides through recrystallization or chromatographic separation.

The n-butyl alcohol/water partition coefficients of several major steviol glycosides in the mother liquor glycosides are shown in Table 1. It can be seen in Table 1 that the polarity difference between rebaudioside A and rebaudioside C and rubusoside is far larger than the polarity difference between rebaudioside A and rebaudioside C and stevioside; and thus, after stevioside is converted into rubusoside, rebaudioside A and rebaudioside C can be separated out of a mixture more easily than before.

TABLE 1

N-butyl alcohol/water partition coefficients of several major steviol glycosides

| | steviol glycosides | | | |
|---|---|---|---|---|
| | stevioside | rebaudioside A | rubusoside | rebaudioside C |
| n-butyl alcohol/ water partition coefficients | 0.36 | 0.09 | 3.5 | 0.2 |

On the other hand, rubusoside (Ru) is a major sweet ingredient in a peculiar rare plant *Rubus suavissimus* S. Lee in China, but the planting area scope is small, the yield is low, and the product is complex in composition and contains a small amount of tannin and other substances. Compared with stevioside, rubusoside only has one β1-2 glucosyl group missing at C13 position, and has a structural formula as follows:

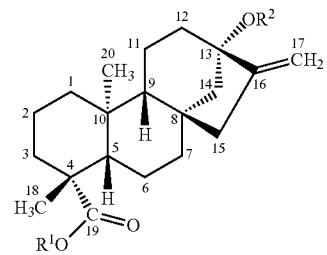

TABLE 2

Structure differences between stevioside and rubusoside

| Name | $R^1$ | $R^2$ |
|---|---|---|
| stevioside (St) | Glc(β1- | Glc(β1-2)Glc(β1- |
| rubusoside (Ru) | Glc(β1- | Glc(β1- |

In general methods of obtaining rubusoside industrially, rubusoside is extracted from leaves of *Rubus suavissimus* S. Lee with a solvent, a product of rubusoside is separated and purified by means of resin or recrystallization, and the obtained rubusoside has a purity of 70-85%. Since the *Rubus suavissimus* S. Lee contains plenty of components, the relatively-high-purity rubusoside cannot be obtained until a solution extracted with the solvent is subjected to a series of processes of filtering, column adsorbing, water washing, ethanol washing, eluant drying and the like (Zhigang Yan, 2017). It causes not only the cost increase, but also wastes due to too low yield.

On the basis of the similarity between stevioside and rubusoside in structure, if glucose at C13 position of stevioside is specifically hydrolyzed, efficient production of rubusoside can be realized. At present, there are two major reported enzymes capable of being used for catalyzing the hydrolysis of stevioside to prepare rubusoside, including β-glucosidase and β-galactosidase. It is found by Ko, et al that the β-glucosidase from *Penicillium decumbens* (Ko, 2013) and *Aspergillus aculeatus* (Ko, 2012) can hydrolyze stevioside to generate rubusoside, but the activity of the two types of β-glucosidase to stevioside is low, so that a proper substrate for the two enzymes may be other glycosides. Wan found the β-galactosidase (Wan, 2012) from *Aspergillus* sp, Chen found the β-galactosidase (Chen, 2014) from *Sulfolobus solfataricus*, Nguyen found the β-galactosidase (Nguyen, 2014) from *Thermus thermophilus*, and the three types of enzymes all have capacity of hydrolyzing stevioside to generate rubusoside; however, these enzymes either show low specificity to stevioside, or show specificity to the Steviosid with a quite high enzyme concentration (2000-14000 U/g stevioside), in which the remained enzymes may introduce a fare amount of unknown proteins and cause adverse effects on food safety control.

In summary, at present, the mother liquor are low in value, and the cost for further separation of rebaudioside A out of the mother liquor glycosides will be higher.

SUMMARY

The disclosure discloses a method to elevate the amount of steviol glycosides remained in the recrystallization mother liquor of *Stevia* extract. In the method, Steviosid in the mother liquor glycosides serves as a substrate, efficiently and specifically converted into rubusoside through lactase (EC3.2.1.23). In this way, the low-value mother liquor glycosides can be converted into the high-value (price) rubusoside, and high-price rebaudioside A can be conveniently separated out of the mother liquor glycosides after the Steviosid in the mother liquor glycosides is converted. Meanwhile, compared with existing preparation methods of rubusoside, the method of the disclosure can avoid the problems that the cost is high and efficiency is low when rubusoside is extracted from leaves of *Rubus suavissimus* S. Lee by means of a solvent method. The *Stevia* mother liquor glycosides are in the mother liquor or a dry product of the mother liquor generated after steviol glycosides extracted and purified in the production of the steviol glycosides, and the *Stevia* mother liquor glycosides contain the stevioside.

Specifically, according to the disclosure, a certain amount of *Stevia* mother liquor glycosides are added into a reactor, lactase from *Kluyveromyces fragilis* is added to reach an enzyme concentration of 10-100 U/g stevioside, the mass of the added lactase does not exceed 1% of the mass of the *Stevia* mother liquor glycosides used, reaction is then performed for 1-3 h at a temperature of 25-45° C., in this process, rebaudioside A does not participate in reaction but continues to stay in the *Stevia* mother liquor glycosides, and rubusoside and rebaudioside A can be separated out after reaction ends.

The *Stevia* mother liquor glycosides may also be replaced with mixed steviol glycosides containing stevioside. The mixed steviol glycosides are extracts of *Rubus suavissimus* S. Lee containing stevioside or a mixture of steviol glycosides with a mass percentage of 1-99.5% of stevioside.

In one embodiment of the disclosure, a solution with a certain concentration is prepared first by adding water to the *Stevia* mother liquor glycosides, and then the lactase is added to catalyze stevioside to generate rubusoside.

In one embodiment of the disclosure, the lactase comes from *Kluyveromyces fragilis*, such as *Kluyveromyces fragilis* (ATCC® 8554).

In one embodiment of the disclosure, an enzyme activity measuring substrate of the lactase is o-nitrophenyl-β-D-galactoside (ONPG).

In one embodiment of the disclosure, the enzyme concentration of the lactase is 10-100 U/g stevioside.

In one embodiment of the disclosure, an enzyme concentration of the lactase is 60 U/g stevioside.

In one embodiment of the disclosure, a reaction temperature is a room temperature, such as 25° C.

In one embodiment of the disclosure, the pH of reaction mixture is 4-6.

By means of the method of directly preparing rubusoside from the mother liquor glycosides provided in the disclosure, high-value utilization of the *Stevia* mother liquor glycosides can be realized, and specifically, the higher-price rubusoside is obtained with stevioside in the low-price mother liquor glycosides as a raw material; after stevioside is hydrolyzed into rubusoside, the original stevioside with a small polarity difference from rebaudioside A in the mother liquor glycosides is converted into rubusoside with a much larger polarity difference from rebaudioside A, and therefore rebaudioside A can be easily obtained; and thus, the value of the *Stevia* mother liquor glycosides is improved.

The disclosure further discloses a method for efficient catalytic conversion of stevioside to synthesize rubusoside. Lactase is adopted for catalytic hydrolysis of stevioside to hydrolyze stevioside into rubusoside. The lactase comes from *Kluyveromyces fragilis*, such as *Kluyveromyces fragilis* (ATCC® 8554).

rebaudioside A in the mother liquor glycosides is extracted in industry by means of a recrystallization method, the recrystallized mother liquor glycosides are complex in composition and contain a large amount of stevioside and rebaudioside A, but it is difficult to separate out and extract stevioside and rebaudioside A due to their small polarity difference, which causes severe waste. By means of the method of directly preparing rubusoside from the mother liquor glycosides provided in the disclosure, lactase is adopted for specific catalytic hydrolysis of stevioside in the *Stevia* mother liquor glycosides to convert stevioside in the *Stevia* mother liquor glycosides into rubusoside which usually can only be obtained from *Rubus suavissimus* S. Lee; and meanwhile, after stevioside in the mother liquor glycosides is converted, the polarity difference between rubusoside and rebaudioside A is far larger than the polarity difference between stevioside and rebaudioside A, and thus the high-quality sweetener rebaudioside A can be more easily separated out of the mother liquor glycosides.

In general, after the above enzymatic treatment, rebaudioside A in enzymatic reaction mixture is extracted by means of an existing process of separating out and extracting rebaudioside A from the mother liquor glycosides, the purity of rebaudioside A is improved, an absolute yield of rebaudioside A can be improved by 25% or above, and a relative yield can be improved by 40% or above.

The lactase used in the disclosure has the capacity of efficiently and specifically hydrolyzing stevioside, and after a conversion rate of stevioside reaches 98.5%, as long as there is no excess enzyme activity, rebaudioside A will not react with rebaudioside C.

The lactase from *Kluyveromyces fragilis* is adopted in the disclosure, and the *Kluyveromyces fragilis* is a microorganism which has been approved to be applied in food additives at present. The lactase has the following advantages: on one hand, the lactase is low in consumption, thereby reducing cost and the content of zymoprotein in reaction products, and thus the product with less impurities is obtained and food safety risks that impure proteins may cause are avoided; and on the other hand, the lactase requires a normal temperature as a reaction temperature and is short in reaction time, thereby reducing the cost burden caused by temperature control.

In summary, the disclosure can efficiently convert the low-value sweetener stevioside into rubusoside in the *Stevia* mother liquor glycosides, the high-purity rebaudioside A and rubusoside can be more easily separated out of the processed Stevia mother liquor glycosides, and thus the high-value application of the Stevia mother liquor glycosides is realized.

BRIEF DESCRIPTION OF FIGURES

FIG. 1A shows that lactase with an enzyme concentration of 60 U/g stevioside is added to a solution of Stevia for reaction for 2 h; and FIG. 1B shows that lactase with an enzyme concentration of 150 U/g stevioside is added to a solution of Stevia for reaction for 2 h.

FIG. 4A shows an HPLC after 50 wt % of rebaudioside A and 50 wt % of stevioside are catalyzed by lactase to react for 2 h at an enzyme concentration of 200 U/g stevioside, where rebaudioside A does not react; FIG. 4B shows an HPLC of rebaudioside A; and FIG. 4C shows an HPLC of 50 wt % of rebaudioside A and 50 wt % of stevioside.

DETAILED DESCRIPTION

A Measurement Method

Figure 1A:
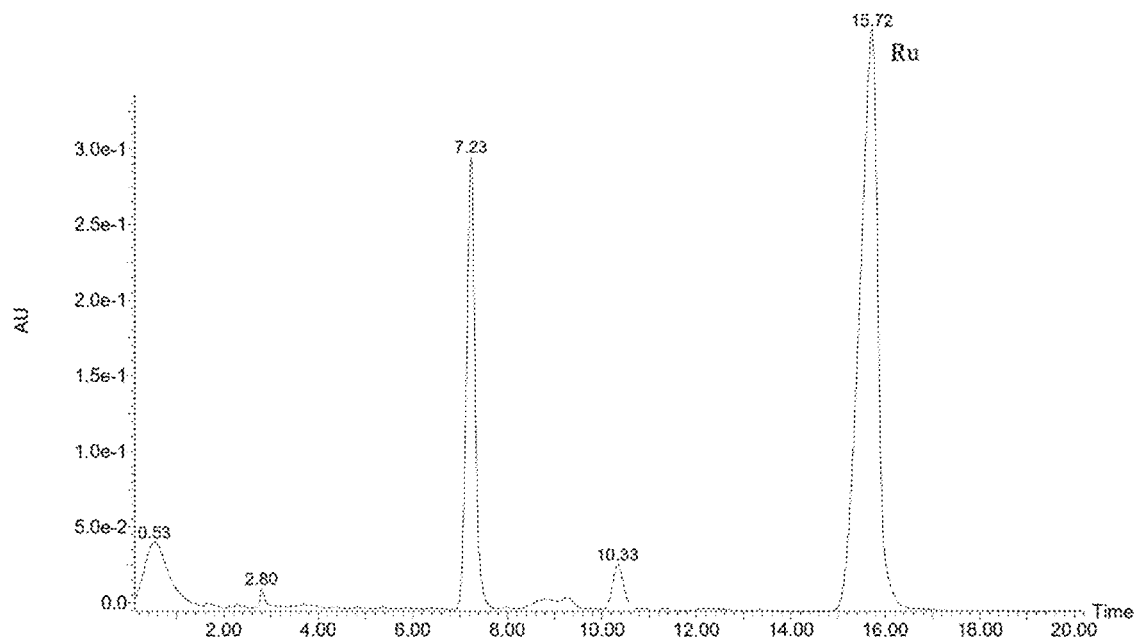
FIG. 1A and FIG. 1B are HPLC of Stevia after enzymatic reaction.

1. Definition of enzyme activity of lactase: with ONPG as a substrate, the lactase performs enzymolysis on the ONPG at a constant temperature of 35° C. and releases an amount of enzyme required by 1 μmol/L o-nitrophenol every minute, which is defined as one enzyme activity unit.

Measurement of enzyme activity of lactase: 500 μL of a pH6.5 phosphate buffer solution and 200 μL of a 0.25% ONPG solution are added into a colorimetric tube for warm bath for 5 min at 35° C., 500 μL of properly-diluted enzyme liquid is added for reaction for 10 min, 800 μL of a 5% $Na_2CO_3$ solution is added to stop reaction, a volume is fixed to 10 mL with distilled water, the absorbance of the solution at 420 nm is measured through an ultraviolet spectrophotometer, and the enzyme activity is calculated according to a standard curve of nitrophenol.

2. Qualitative Analysis of Steviol Glycosides

Qualitative analysis is performed on hydrolysis and transglucosyl products through a liquid chromatography tandem quadrupole rod time-of-flight mass spectrometer, and the detection conditions include: a Kromasil 100-5-C18 chromatographic column (4.6*250 mm), a column temperature of 40° C., acetonitrile to water=32:68 (v/v) for isocratic elusion, a sample size of 10 μL, a sample injection concentration of 10 mg/mL, and a flowing velocity of 1 mL/min; a mass spectrometry condition: a fragmentor voltage of 6 eV; an ionization mode: electrospray ionization (ESI), an anion detection mode, and a molecular weight of 200-2000.

3. Quantitative Analysis of Steviol Glycosides

A standard curve is drawn with rebaudioside A (HPLC 99%) as a standard sample, concentrations of rebaudioside A, stevioside and rubusoside are figured out through the standard curve of rebaudioside A by means of an analysis and detection method of steviol glycosides in JECFA2016.

A conversion rate calculation formula of stevioside:

$$\alpha = [(C_0 - C_t)/C_0] \times 100\% \quad (1)$$

where α represents a conversion rate of stevioside, $C_0$ represents a concentration of stevioside when a solution does not react, and $C_t$ represents a concentration of stevioside in reaction mixture at time t.

A yield calculation formula of rubusoside:

$$\beta = (C_m/C_n) \times 100\% \quad (2)$$

where β represents a yield of rubusoside, $C_m$ represents a concentration of rubusoside when reaction ends, and $C_n$ represents a concentration of rubusoside that can be produced theoretically. $C_m$ and $C_n$ are both figured out by means of a method disclosed in JECFA2016.

rubusoside yield=(mass of rubusoside obtained after separation and purification of each gram of raw material/mass of rubusoside that can be produced from each gram of raw material theoretically)*100%

Example 1 A Preparation Method of Lactase from Kluyveromyces fragilis (ATCC® 8554)

A strain of Kluyveromyces fragilis (ATCC® 8554) is inoculated into a YPD agar slant culture medium for shake cultivation at 30° C. Then, 10% of a cultivated seed culture solution is inoculated into a liquid fermentation culture medium (containing lactose and yeast powder) for shake cultivation at 28° C. at 180 rpm for 36 h. The fermentation culture is then centrifuged for 15 min at 4000 r/min. After discasted the supernatant, phosphate buffer (pH7.0) is added to the deposited yeast cells, stirred and then processed by a ball mill at 180 r/min for 60 min. Triple volume of phosphate buffer solution (pH7.0) is then added, stirred to even, flowed by centrifuge to remove the yeast cell fragments; and then the crude enzyme can be obtained. A ultrafiltration membrane with a molecular weight cut-off of 30 kDa is used, the crude enzyme is subjected to ultrafiltration under pressure of 70 KPa to obtain a concentrated solution. The membrane is washed with a buffer solution. The concentrated solution and the washing solution are combined to obtain a concentrated enzyme solution, and the concentrated enzyme solution is freeze-dried to obtain freeze-dried powder with a specific enzyme activity of 40000 U/g.

Example 2 Preparation of Rubusoside from Stevia Mother Liquor Glycosides and Further Separation of Rebaudioside A A Stevia mother liquor glycoside solution (19% of rebaudioside A, 66% of stevioside and 9% of rebaudioside C) obtained as the residue from recrystallization of rebaudioside A, is then concentrated to reach a solid content of 300 g/L. The lactase obtained from Example 1 is added to reach an enzyme concentration of 100 U/g stevioside for reaction at 30° C. for 2 h. The reaction mixture is dried and then recrystallized with 95% ethanol to separate out rubusoside with a purity of 97.1% and a yield of 88.9%, and rebaudioside A is separated out with a purity of 95.8% and a yield of 86%.

Comparative Example 1

Stevia mother liquor glycoside solid (19% of rebaudioside A, 66% of stevioside and 9% of rebaudioside C) obtained as the residue from recrystallization of rebaudioside A is recrystallized with 95% ethanol to separate out rebaudioside A, the purity is 84.2% and the yield is 54.9%.

Compared with Example 2, it can be seen that by converting the mother liquor glycosides through an enzyme method recorded in Example 2, the purity of rebaudioside A can be improved, an absolute yield of rebaudioside A is improved by 31.1%, and a relative yield is improved by 56.6%.

Example 3 Preparation of Rubusoside from Stevia Mother Liquor Glycosides and Further Separation of Rebaudioside A A Stevia mother liquor glycoside solution (33% of rebaudioside A, 41% of stevioside and 11% of rebaudioside C), as a by-product during refining of rebaudioside A, is concentrated to reach a solid content of 30%. The lactase obtained in Example 1 is added to reach an enzyme concentration of 80 U/g stevioside for reaction at 30° C. for 1 h. The reaction mixture is spray-dried and then recrystallized with 95% ethanol to separate out rubusoside. The obtained rubusoside possess a purity of 96.7% and a yield of 91.7%, and rebaudioside A is separated out with a purity of 95.7% and a yield of 87.2%.

Comparative Example 2

Stevia mother liquor glycosides (33% of rebaudioside A, 41% of stevioside and 11% of rebaudioside C), as by-products of refining of rebaudioside A, are spray-dried and then recrystallized with 95% ethanol to separate out rebaudioside A, the obtained RA possess a purity of 86.2% and a yield of 61.8%

Compared with Example 3, it can be seen that by converting mother liquor glycosides through an enzyme method recorded in Example 3, the purity of rebaudioside A can be improved, an absolute yield of rebaudioside A is improved by 25.4%, and a relative yield is improved by 41.1%.

Example 4 Preparation of Rubusoside from Stevia Sugar 250 g/L glycoside liquid is prepared with deionized water from Stevia sugar (containing 22% of rebaudioside A, 68% of stevioside and 3% of rebaudioside C in percentages by mass). The lactase freeze-dried powder obtained in Example 1 is added to reach an enzyme concentration of 60 U/g stevioside for reaction at 35° C. for 2 h. The reaction mixture is analyzed through a high performance liquid chromatograph, the HPLC profile of the product is shown in FIG. 1A, a conversion rate of stevioside reaches 98.3%, and a yield of rubusoside is 97.7%.

Comparative Example 3

Figure 1B:
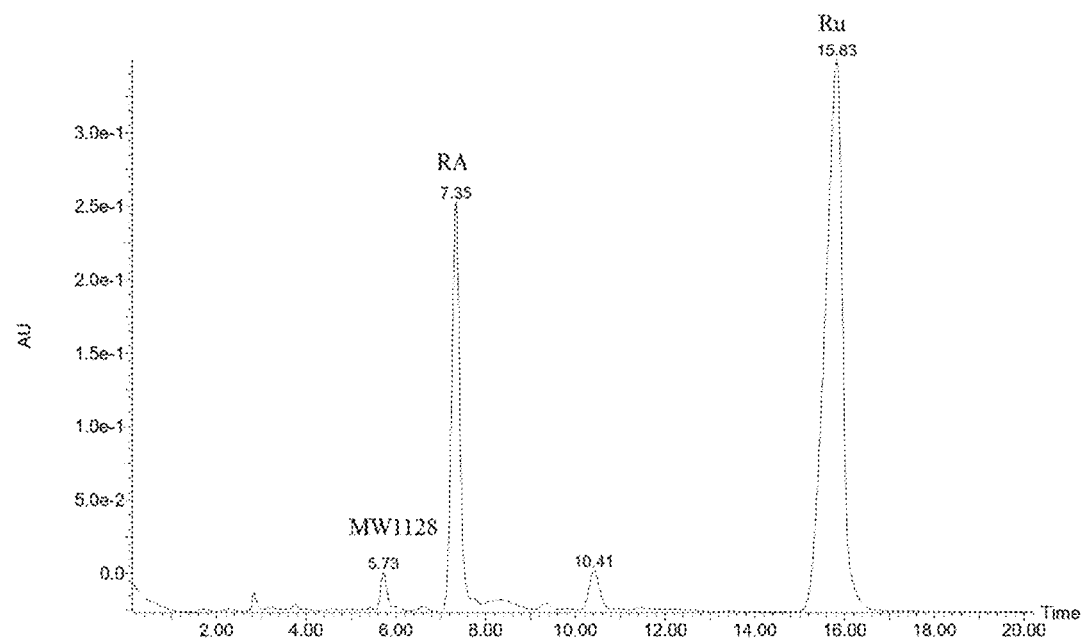

250 g/L glycoside liquid is prepared with deionized water from Stevia sugar (containing 22% of rebaudioside A, 68% of stevioside and 3% of rebaudioside C in percentages by mass). The lactase freeze-dried powder obtained in Example 1 is added to reach an enzyme concentration of 150 U/g stevioside for reaction at 35° C. for 24 h. The reaction mixture is analyzed through the high performance liquid chromatograph, the HPLC profile of the product is shown in FIG. 1 (b), a conversion rate of stevioside reaches 99.5%, and a yield of rubusoside is 89.1%. It can be seen in FIG. 1B that transglucosyl products are generated when an enzyme concentration of the lactase is too high and an LC-MS analysis result shows that a molecular weight of the transglucosyl products conforms to that of St-Glc2 or RA-Glc1.

Figure 2:
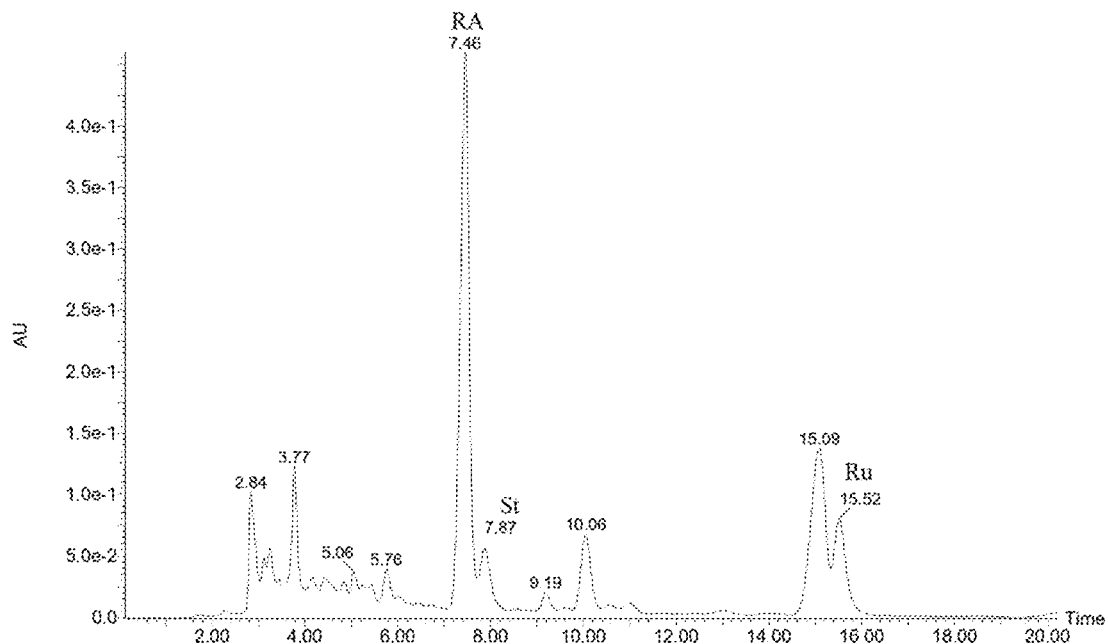
FIG. 2 is an HPLC of reaction mixture obtained after lactase with an enzyme concentration of 30 U/g stevioside is added to a solution of mother liquor glycosides for reaction for 2 h.

Example 5 Preparation of Rubusoside from Stevia Mother Liquor Glycosides 100 g/L glycoside liquid is prepared from the Stevia mother liquor glycosides (containing 47% of rebaudioside A, 19% of stevioside and 7% of rebaudioside C in percentages by mass). The lactase freeze-dried powder obtained in Example 1 is added to reach an enzyme concentration of 30 U/g stevioside for reaction at 25° C. for 0.5 h. The reaction mixture is analyzed through the high performance liquid chromatograph, the HPLC profile of the reaction mixture is shown in FIG. 2; a conversion rate of stevioside reaches 72.7%, and a yield of rubusoside is 70.5%. It can be seen that a conversion rate of stevioside will drop at a low temperature, a low enzyme concentration and a short reaction time.

Example 6 Preparation of Rubusoside from Stevioside

Figure 3:
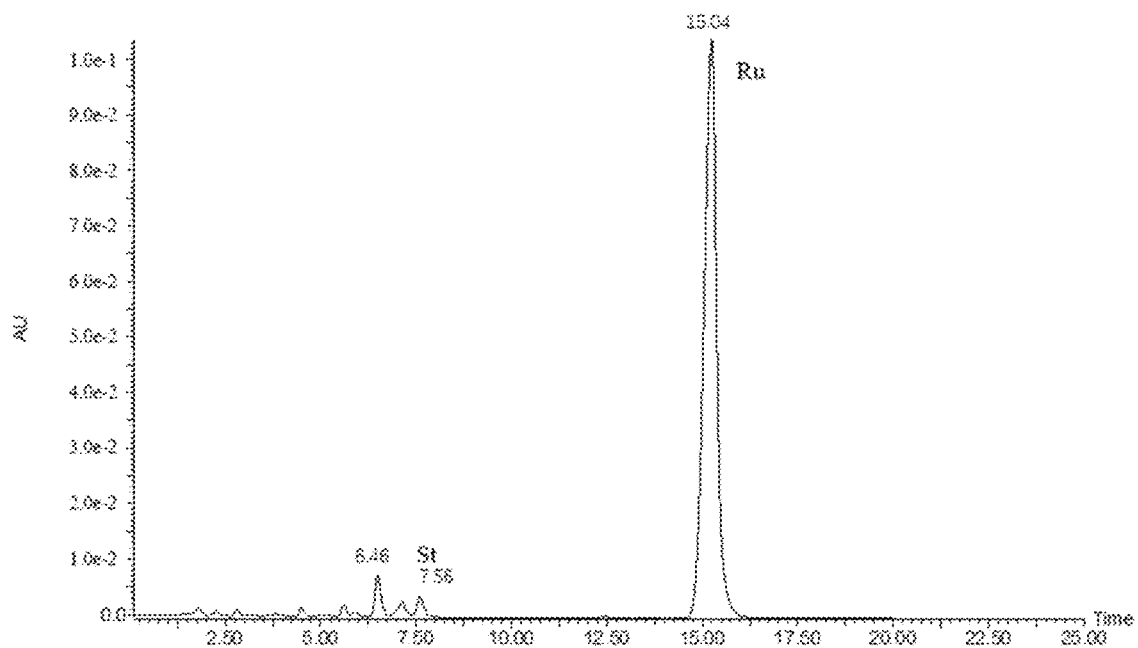
FIG. 3 is an HPLC of reaction mixture obtained after stevioside is catalyzed by lactase to react for 2 h.

A 200 g/L stevioside solution is prepared by dissolving 20 g of stevioside (97%, HPLC) in 100 mL of deionized water into a reactor. The lactase freeze-dried powder obtained in Example 1 is added to reach an enzyme concentration of 90 U/g stevioside for reaction at 35° C. for 2 h. The reaction mixture is analyzed through the high performance liquid chromatograph, the HPLC profile of the product is shown in FIG. 3, a conversion rate of stevioside reaches 98.9%, and a yield of rubusoside is 97.9%.

Comparative Example 4

Figure 4A:
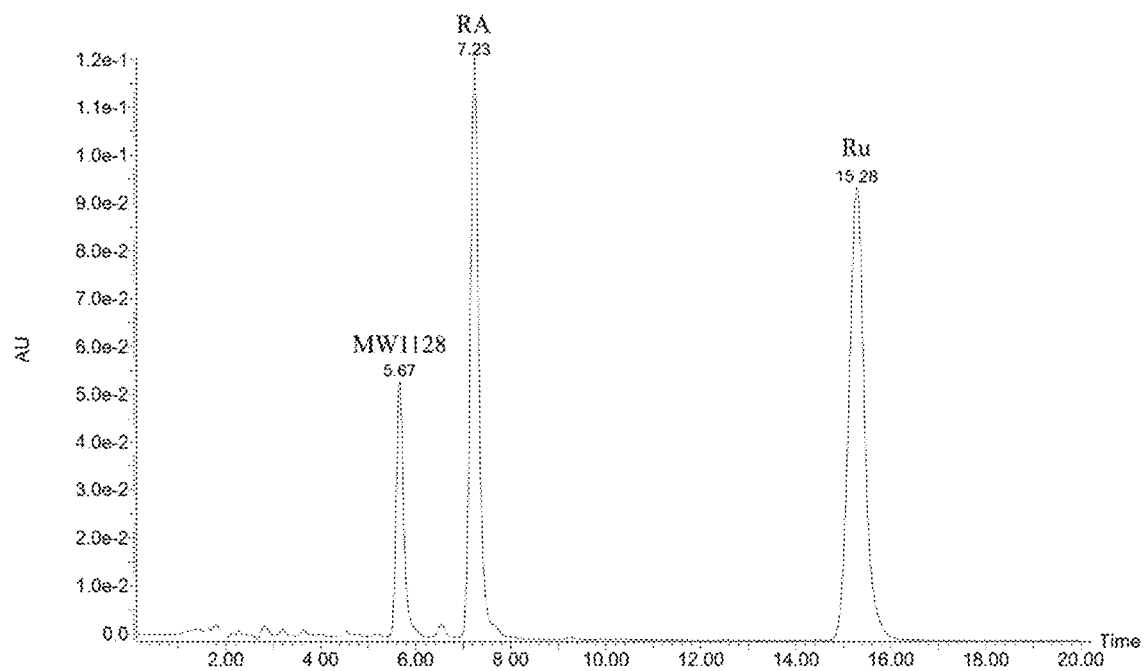
FIG. 4A-FIG. 4C are an HPLC after rebaudioside A itself or a mixture of rebaudioside A and stevioside is catalyzed by lactase to react.

The lactase freeze-dried powder obtained in Example 1 is added to a mixed glycoside solution (50% of stevioside and 50% of rebaudioside A) with a solid content of 200 g/L to reach an enzyme concentration of 200 U/g stevioside, stirred at 35° C. for 2 h. The reaction mixture is analyzed through the high performance liquid chromatograph, a conversion rate of stevioside reaches 99.5%, a yield of rubusoside is 83%, the HPLC profile of the product is shown in FIG. 4A, transglucosyl products are produced, and a molecular weight of the transglucosyl products is 1128 as measured by LC-MS analysis.

Figure 4B:
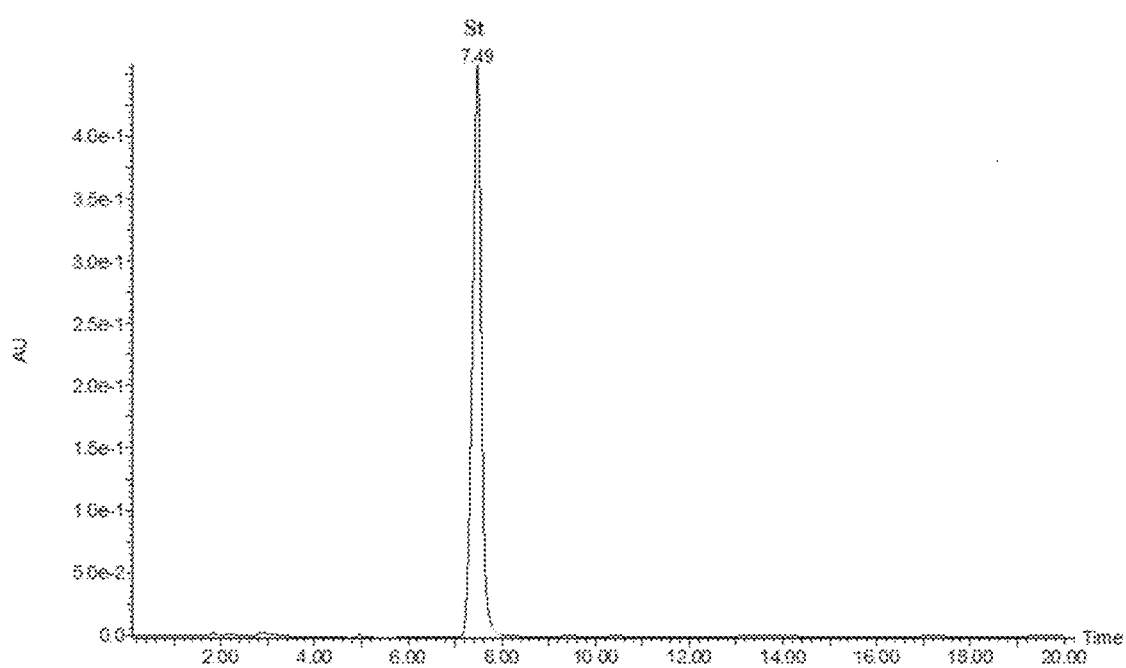
Figure 4C:
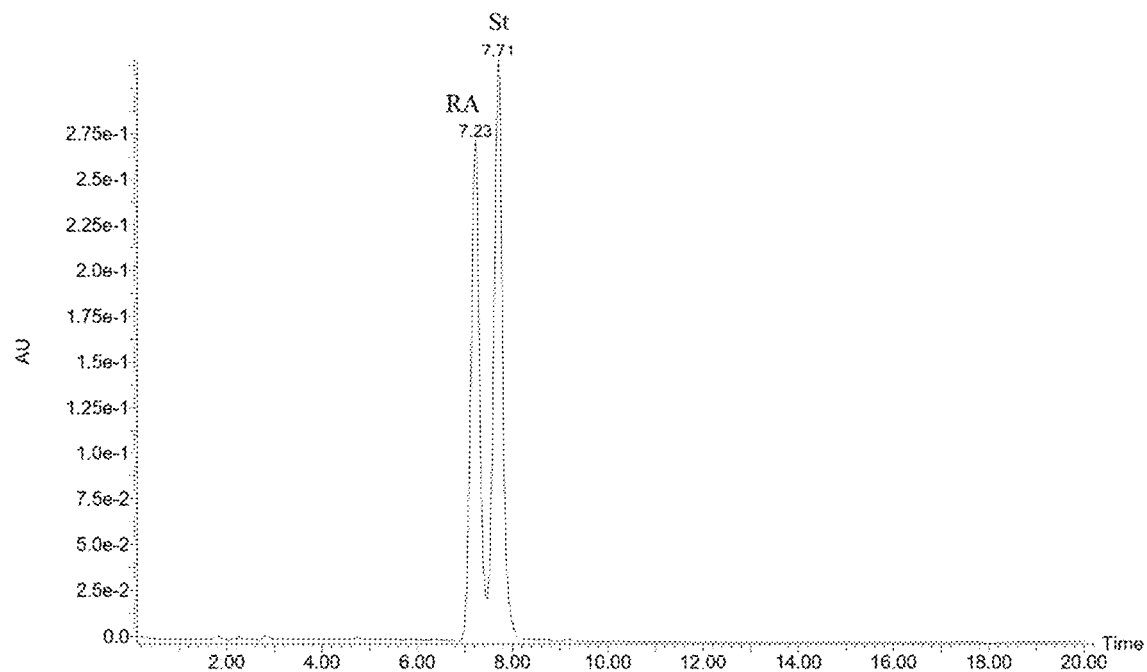

A 20 mg/mL solution of stevioside (97%, HPLC) and a 20 mg/mL 50 wt % rebaudioside A+50 wt % stevioside are prepared respectively, the two types of glycoside liquid is analyzed through the high performance liquid chromatograph respectively, and HPLC profiles of the two glycoside liquids are shown in FIG. 4B and FIG. 4C, respectively.

Comparative Example 5

Figure 5:
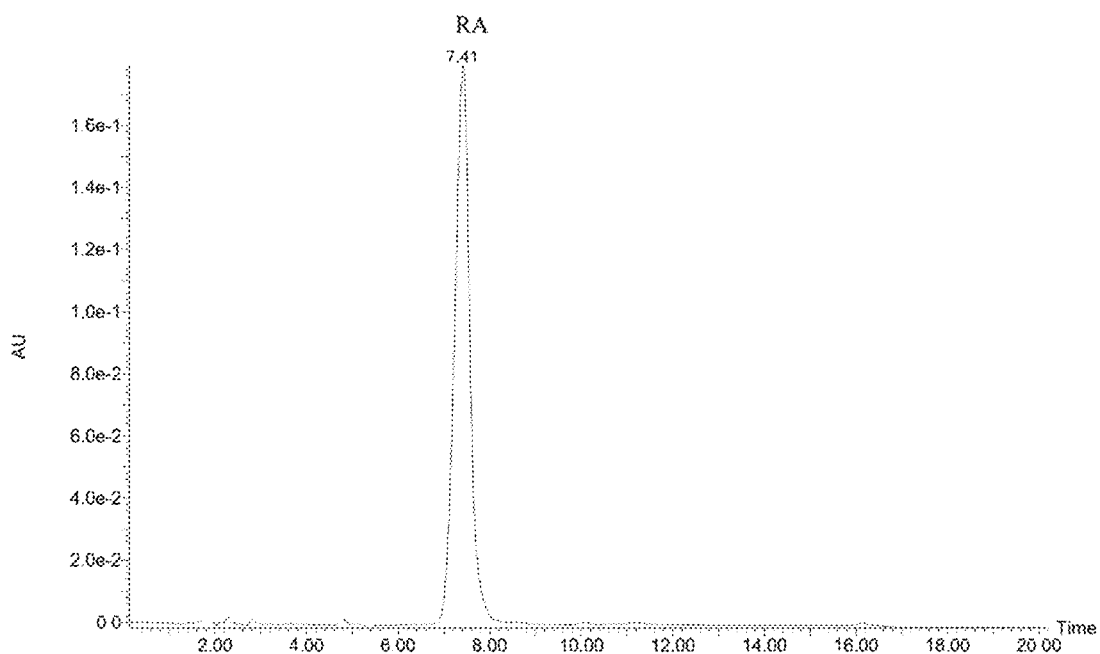
FIG. 5 is an HPLC after rebaudioside A and lactase coexist for 2 h.

A 10 g/L rebaudioside A solution is prepared by dissolving 1 g of rebaudioside A (99%, HPLC) in 100 mL of deionized water and preheated for 30 min at 30° C. The lactase freeze-dried powder obtained in Example 1 is added to reach an enzyme concentration of 100 U/g rebaudioside A for reaction for 24 h at 30° C. The reaction mixture is analyzed through the high performance liquid chromatograph, the HPLC profile of the product is shown in FIG. 5, and rebaudioside A did not react.

Comparative Example 6

450 g/L glycoside liquid is prepared with a pH5 phosphate-potassium phosphate buffer solution (50 mmol/L)

from *Stevia* sugar (containing 22% of rebaudioside A, 68% of stevioside and 3% of rebaudioside C in percentages by mass). The lactase (Lactozym Pure 7500 L, purchased from Novozymes company in China) is added to reach an enzyme concentration of 100 U/g stevioside for reaction at 30° C. for 2 h. Then, the reaction mixture is analyzed through the high performance liquid chromatograph, and the results show that there is no rubusoside produced in the reaction mixture and stevioside was not converted either.

Comparative Example 7

450 g/L glycoside liquid is prepared with a pH5 phosphate-potassium phosphate buffer solution (50 mmol/L) from *Stevia* sugar (containing 22% of rebaudioside A, 68% of stevioside and 3% of rebaudioside C in percentages by mass). The lactase (trade name: Lactozym 3000 L HP-G, purchased from Novozymes company in China) from *Kluyveromyces lactis* is added to reach an enzyme concentration of 100 U/g stevioside for reaction at 30° C. for 2 h. Then, the reaction mixture is analyzed through the high performance liquid chromatograph, and the results show that the content of stevioside in the reaction mixture is not reduced, stevioside is not converted and there is no rubusoside produced.

Comparative Example 8

450 g/L glycoside liquid is prepared with a pH5 phosphate-potassium phosphate buffer solution (50 mmol/L) from *Stevia* sugar (containing 22% of rebaudioside A, 68% of stevioside and 3% of rebaudioside C in percentages by mass). The lactase (trade name: Maxilact LG 2000, purchased from Royal DSM company in N.V.) from *Kluyveromyces lactis* is added to reach an enzyme concentration of 100 U/g stevioside for reaction at 30° C. for 2 h. Then, the reaction mixture is analyzed through the high performance liquid chromatograph; and the results show that the content of stevioside in the reaction mixture has no change and there is no rubusoside produced, indicating that stevioside is not converted. However, if reaction time is regulated from 2 h to 20 h, there is still no rubusoside produced, but steviolbioside is produced.

Comparative Example 9

450 g/L glycoside liquid is prepared with a pH5 phosphate-potassium phosphate buffer solution (50 mmol/L) from *Stevia* sugar (containing 22% of rebaudioside A, 68% of stevioside and 3% of rebaudioside C in percentages by mass). The lactase from *Aspergillus niger* (ATCC® 9029™) is added to reach an enzyme concentration of 100 U/g stevioside for reaction at 30° C. for 2 h. Then, the reaction mixture is analyzed through the high performance liquid chromatograph, and the results show that the content of stevioside in the reaction mixture has no change and there is no rubusoside produced.

What is claimed is:

1. A method of preparing rubusoside from *Stevia* mother liquor glycosides, comprising:
    adding lactase from *Kluyveromyces fragilis* to the *Stevia* mother liquor glycosides and incubating for 1 to 3 hours at a temperature of 25° C. to 45° C. for specific catalytic hydrolysis of stevioside in the *Stevia* mother liquor glycosides, so that stevioside is hydrolyzed into rubusoside, wherein rebaudioside A remains in the *Stevia* mother liquor glycosides and is not acted upon by the lactase; and
    separating rubusoside and rebaudioside A, wherein other steviol glycosides including rebaudioside A are separated excluding rubusoside through exclusion chromatography or recrystallization;
    wherein an enzyme concentration of the lactase is 10 U/g to 100 U/g stevioside, and mass of the added lactase does not exceed 1% of mass of the *Stevia* mother liquor glycosides-used.

2. The method according to claim 1, wherein the *Stevia* mother liquor glycosides are mother liquor or a dry product of the mother liquor generated after the steviol glycosides are extracted or purified in a process of extracting the steviol glycosides from *Stevia rebaudiana* leaves.

3. The method according to claim 2, wherein the enzyme concentration of the lactase is 10U/g to 60 U/g stevioside.

4. The method according to claim 3, wherein pH of the substrate is 4 to 6 during the catalytic reaction with the lactase.

5. The method according to claim 1, wherein the *Stevia* mother liquor glycosides is replaced with mixed steviol glycosides containing stevioside.

6. The method according to claim 1, wherein a solution with a predetermined concentration is prepared first by adding water to the *Stevia* mother liquor glycosides, and then the lactase is added to catalyze stevioside to produce rubusoside; and a mass concentration of steviol glycosides in an aqueous solution of the *Stevia* mother liquor glycosides is 100 g/L to 500 g/L.

7. The method of claim 1, further comprising: separating rubusoside and rebaudioside A by spray-drying and then recrystallizing in 95% ethanol to separate out rubusoside.

8. A method of converting stevioside to rubusoside, comprising:
    incubating lactase from *Kluyveromyces fragilis* with stevioside to hydrolyze stevioside into rubusoside.

9. The method according to claim 8, wherein the lactase comes from *Kluyveromyces fragilis*, the lactase exists in a form of a concentrated solution, freeze-dried powder or an immobilized enzyme, and an enzyme concentration does not exceed 1% of mass of *Stevia* mother liquor glycosides used.

10. The method according to claim 8, wherein the reaction is performed for 1 to 3 hours at a temperature of 25° C. to 45° C.

11. The method according to claim 9, wherein the reaction is performed for 1to 3 hours at a temperature of 25° C. to 45° C.

12. The method according to claim 10, wherein the reaction is performed for 2to 3 hours at a temperature of 30° C.

* * * * *